(12) United States Patent
Bange et al.

(10) Patent No.: US 8,394,927 B2
(45) Date of Patent: Mar. 12, 2013

(54) FGFR4 ANTIBODIES

(75) Inventors: Johannes Bange, Planegg (DE); Jens Niewoehner, Munich (DE); Patricia Aus Dem Siepen, Feldafing (DE); Mike Rothe, Krailling (DE)

(73) Assignee: U3 Pharma GmbH, Martinsried (DE)

( * ) Notice: Subject to any disclaimer, the term of this patent is extended or adjusted under 35 U.S.C. 154(b) by 339 days.

(21) Appl. No.: 12/513,448

(22) PCT Filed: Nov. 2, 2007

(86) PCT No.: PCT/EP2007/009530
§ 371 (c)(1),
(2), (4) Date: Mar. 5, 2010

(87) PCT Pub. No.: WO2008/052796
PCT Pub. Date: May 8, 2008

(65) Prior Publication Data
US 2010/0169992 A1    Jul. 1, 2010

(30) Foreign Application Priority Data
Nov. 3, 2006 (EP) .................................... 06022938

(51) Int. Cl.
*C12P 21/08* (2006.01)
(52) U.S. Cl. .................... 530/387.3; 530/391.3
(58) Field of Classification Search .............. None
See application file for complete search history.

(56) References Cited

U.S. PATENT DOCUMENTS
2005/0152910 A1* 7/2005 Chermann et al. ......... 424/159.1

FOREIGN PATENT DOCUMENTS
| EP | 1 332 761 A | 8/2003 |
|---|---|---|
| WO | 02/102854 A | 12/2002 |
| WO | 2005/066211 A | 7/2005 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
Mawrin et al: "Analysis of a single nucleotide polymorphism i n codon 388 of the FGFR4 gene i n malignant gliomas" Cancer Letters, New York, NY, US, vol. 239, No. 2, Aug. 8, 2006, pp. 239-245, Abstract.
Vainikka Satu et al: "Fibroblast growth factor receptor-4 shows novel features in genomic structure, ligand binding and signal transduction" EMBO (European Molecular Biology Organization) Journal, vol. 11, No. 12, 1992, pp. 4273-4280.
Eswarakumar V P et al: "Cellular signaling by fibroblast growth factor receptors" Cytokine and Growth Factor Reviews, Oxford, GB, vol. 16, No. 2, Apr. 2005, pp. 139-149, Abstract.
Chen Chaoyuan et al: "Generation and characterization of a panel of monoclonal antibodies specific f o r human fibroblast growth factor receptor 4 (FGFR4)." Hybridoma Jun. 2005, vol. 24, No. 3, Jun. 2005, pp. 152-159, Abstract.
Chen Chaoyuan (Charlie): "Murine MAbs specific for the extracellular domain of human fibroblast growth factor receptor 4 (FGFR4-ECD) and reactive with the native form of human FGFR4" Hybridoma, vol. 24, No. 3, Jun. 2005, pp. 168-169.
Kiss et al., "Antibody binding loop insertions as diversity elements", Nucleic Acid Research, vol. 34, No. 19, published online on Oct. 5, 2006, pp. e132.
Hey et al., "Artificial, non-antibody binding proteins for pharmaceutical and industrial applications", Trends in Biotechnology, vol. 23, No. 10, Oct. 2005, pp. 514-522.
European Search Report dated Feb. 27, 2012 based on application European application No. 11181248.3-2406, 10 pages.

* cited by examiner

*Primary Examiner* — Brad Duffy
(74) *Attorney, Agent, or Firm* — Rothwell, Figg, Ernst & Manbeck, P.C.

(57) ABSTRACT

The present invention relates to FGFR4 antibodies including fragments or derivatives thereof and the polynucleotides encoding the antibodies. Expression vectors and host cells comprising the polynucleotides are provided. Further, the invention refers to pharmaceutical compositions comprising the FGFR4 antibodies and methods for the treatment, prevention or diagnosis of disorders associated with FGFR4 expression.

15 Claims, 5 Drawing Sheets

FGFR4 ANTIBODIES

CROSS REFERENCE TO RELATED APPLICATION

Figure 1:
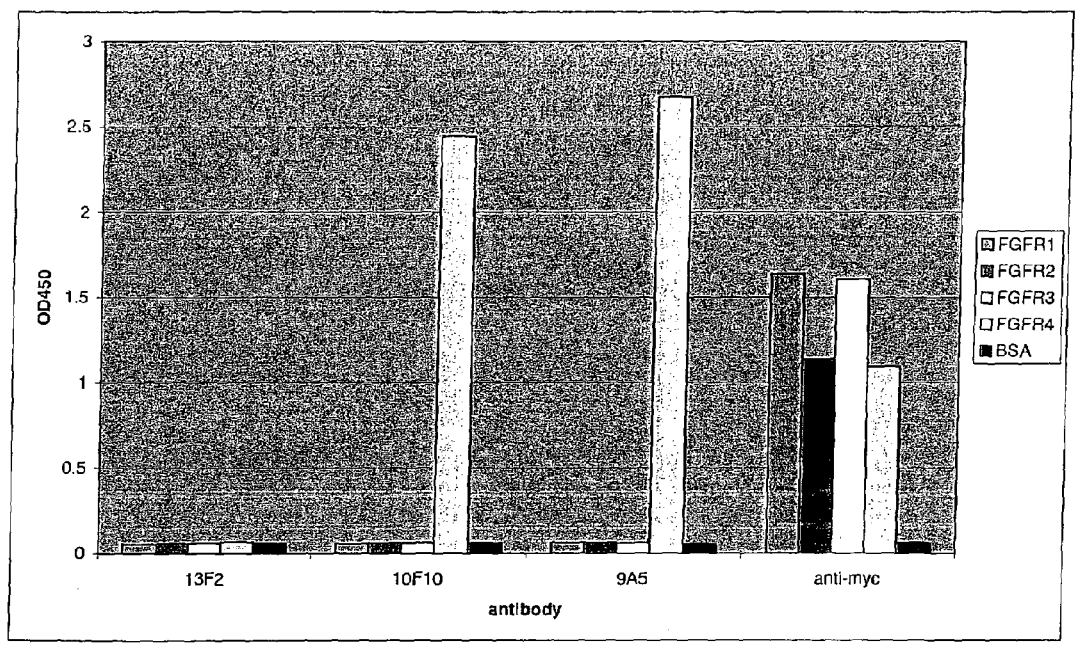

This application is a 35 U.S.C. 371 National Phase Entry Application from PCT/EP2007/009530, filed Nov. 2, 2007, which claims the benefit of European Patent Application No. 06022938.2 filed on Nov. 3, 2006, the disclosure of which is incorporated herein in its entirety by reference.

The present invention relates to FGFR4 antibodies including fragments or derivatives thereof and the polynucleotides encoding the antibodies. Expression vectors and host cells comprising the polynucleotides are provided. Further, the invention refers to pharmaceutical compositions comprising the FGFR4 antibodies and methods for the treatment, prevention or diagnosis of disorders associated with FGFR4 expression.

The Fibroblast Growth Factor Receptor 4 (FGFR4) belongs to the family of FGF receptors which also includes FGFR1, FGFR2 and FGFR3. Like the other members of the FGF receptor family, the transmembrane receptor FGFR4 consists of an extracellular ligand-binding domain (ECD), a transmembrane domain, an intracellular protein tyrosine kinase domain (TKD) and a C-terminal phosphorylation domain (Klint P et al., 1998).

The FGF receptors are activated by the family of fibroblast growth factors (FGF), comprising 23 members to date (Eswarakumar et al., 2005; Yamashita, 2005). In contrast to FGFR4, where only two splice variants are known, other family members such as FGFR1, 2 and 3 can be altered in their affinity for different FGFs by multiple splice variations (van Heumen et al., 1999).

FGFR4 is activated by FGF1, FGF2, FGF4, FGF6, FGF8 and FGF9 with decreasing efficiency (Ornitz et al., 1996); while all of these activate also other family members, FGF19 is specific for FGFR4 (Xie et al., 1999). Activation of the receptor by FGFs requires binding of the ligand to heparin; interestingly, FGFR4 can also be activated by heparin alone (Gao and Goldfarb, 1995). Many FGFs are broad-spectrum mitogens, whereas some induce cell motility, or alter the state of cellular differentiation (for review McKeehan W L, et al., 1998). In vivo, some FGFs have potent angiogenic properties, and others have been implicated in tissue remodeling, such as that required for wound repair (Werner S, et al., 1994).

Upon binding of the ligand to the extracellular domain of FGFR4, receptor dimerization and subsequent phosphorylation of tyrosine kinase residues results in activation of signaling pathways by inducing the binding of signaling molecules to the receptor (Vainikka et al., 1992); (Vainikka et al., 1994). For example FGFR4 associates with PLC-γ1, and an increase in MAP kinase activation and DNA synthesis upon a FGF stimulation has been observed. Further interaction with other human FGF growth factor receptor family members may expand the signaling potential of FGFR4 and is a means not only for signal diversification but also signal amplification (McKeehan W L, & Kan M, 1994). An 85-kDa serine kinase has been found to negatively regulate tyrosine phosphorylation of FGFR4, but its exact function has not been elucidated (Vainikka et al., 1996). Association of FGFR4 with NCAM has been demonstrated to mediate integrin-dependent adhesion (Cavallaro et al., 2001), which might play a decisive role in tumor metastasis.

FGFR4 has been reported to inhibit myogenic differentiation (Shaoul et al., 1995), and although muscle development appears to be normal in FGFR4 knockout animals (Weinstein et al., 1998), muscle regeneration after cardiotoxin-induced damage was shown to be impaired (Zhao et al., 2006). FGFR3/FGFR4 double knockouts are impaired in secondary septation during alveolus formation, leading to immature lungs (Weinstein et al., 1998). The defect is not observed in FGFR3 knockout mice, which only show skeletal defects. The phenotype of FGFR4 single knockout mice is increased bile acid synthesis, accompanied by hepatomegaly under high-cholesterol diet (Yu et al., 2000).

FGFR4 has been found to be expressed and/or influencing prognostic outcome in several types of cancer such as melanoma (Streit et al., 2006), breast (Jaakola et al., 1993), prostate (Wang et al., 2004), thyroid (Bernard et al., 2005) and pancreatic cancers (Leung et al., 1994). In addition a polymorphism at position 388 of the polypeptide sequence is associated with a more aggressive disease status in melanoma (Streit et al., 2006), breast (Bange et al, 2002), prostate (Wang et al., 2004), HNSCC (Streit et al., 2004), lung adenocarcinoma (Spinola et al., 2005) and soft tissue sarcoma (Morimoto et al., 2003).

Interestingly, transgenic expression of the FGFR4 specific ligand FGF19 under control of a muscle-specific promoter in mice has been found to lead to hepatocellular carcinoma (Nicholes et al., 2002).

Accordingly, agents that interfere with FGFR4 mediated signaling are desirable. FGFR4 antibodies have been reported, such as in WO 03/063893 and WO 99/37299.

An effective strategy to target tumor cells, that is based on the discovery of the mechanisms of tumor development, is the usage of monoclonal antibodies. For example Herceptin™, an antibody directed against the receptor tyrosine kinase HER2, improves the median survival rate of breast cancer patients by approximately 25% compared with chemotherapy alone, and has only very mild side effects. Other strategies to use monoclonal antibodies in tumor therapy include immunotoxins, like Mylotarg™, a recombinant IgG4 kappa antibody conjugated to calicheamicin, and antibodies labelled with radioisotopes, as for example Zevalin™.

In order to provide further products for diagnostic and/or therapeutic applications it is desirable to have FGFR4 antibodies that bind specifically to the extracellular domain and block FGFR4 mediated signal transduction.

Thus the technical problem underlying the present invention was to provide novel FGFR4 antibodies and methods of use of the same which are suitable for diagnosing, preventing and/or treatment of diseases associated with FGFR4 expression.

The solution of the above problems is achieved by providing the embodiments characterized in the claims.

A first aspect of the present invention relates to an antibody including a fragment or derivative thereof that binds to the extracellular domain of FGFR4, particularly of human FGFR4, and at least partially inhibits FGFR4 activity.

Preferably, the antibody has at least one antigen binding site, e.g. one or two antigen binding sites. Further, the antibody preferably comprises at least one heavy immunoglobulin chain and at least one light immunoglobulin chain. An immunoglobulin chain comprises a variable domain and optionally a constant domain. A variable domain may comprise complementary determining regions (CDRs), e.g. a CDR1, CDR2 and/or CDR3 region, and framework regions. The term "complementary determining region" (CDR) is well-defined in the art (see, for example, Harlow and Lane, "Antibodies, a laboratory manual", CSH Press, Cold Spring Harbour, 1988) and refers to the stretches of amino acids within the variable region of an antibody that primarily makes contact with the antigen.

A second aspect of the present invention relates to an antibody including a fragment or derivative thereof that binds to the extracellular domain of FGFR4 and which comprises at least one heavy chain amino acid sequence comprising at least one CDR selected from the group consisting of:
(a) CDRH1 as shown in SEQ ID NOs: 9 or 15, or a CDRH1 sequence differing in 1 or amino acids therefrom,
(b) a CDRH2 as shown in SEQ ID NOs: 10 or 16, or a CDRH2 sequence differing in 1 or 2 amino acids therefrom, and
(c) a CDRH3 as shown in SEQ ID NOs: 11 or 17, or a CDRH3 sequence differing in 1 or 2 amino acids therefrom, and/or at least one light chain amino acid sequence comprising at least one CDR selected from the group consisting of:
(d) a CDRL1 as shown in SEQ ID NOs: 12 or 18, or a CDRL1 sequence differing in 1 or 2 amino acids therefrom,
(e) a CDRL2 as shown in SEQ ID NOs: 13 or 19, or a CDRL2 sequence differing in 1 or 2 amino acids therefrom, and
(f) a CDRL3 as shown in SEQ ID NOs: 14 or 20, or a CDRL3 sequence differing in 1 or 2 amino acids therefrom,
or an antibody recognizing the same epitope on the extracellular domain of FGFR4.

In a preferred embodiment, the antibody comprises at least one heavy chain comprising at least one CDR selected from the group consisting of
(a) a CDRH1 as shown in SEQ ID NO: 9, or a CDRH1 sequence differing in 1 or 2 amino acids therefrom,
(b) a CDRH2 as shown in SEQ ID NO: 10, or a CDRH2 sequence differing in 1 or 2 amino acids therefrom, and
(c) a CDRH3 as shown in SEQ ID NO: 11, or a CDRH3 sequence differing in 1 or 2 amino acids therefrom, and/or
a light chain comprising at least one CDR selected from the group consisting of
(d) a CDRL1 as shown in SEQ ID NO: 12, or a CDRL1 sequence differing in 1 or 2 amino acids therefrom,
(e) a CDRL2 as shown in SEQ ID NO: 13, or a CDRL2 sequence differing in 1 or 2 amino acids therefrom, and
(f) a CDRL3 as shown in SEQ ID NO: 14, or a CDRL3 sequence differing in 1 or 2 amino acids therefrom, or an antibody recognizing the same epitope on the extracellular domain of FGFR4.

In a further preferred embodiment, the antibody comprises a heavy chain comprising at least one CDR selected from the group consisting of
(a) a CDRH1 as shown in SEQ ID NO: 15, or a CDRH1 sequence differing in 1 or 2 amino acids therefrom,
(b) a CDRH2 as shown in SEQ ID NO: 16, or a CDRH2 sequence differing in 1 or 2 amino acids therefrom, and
(c) a CDRH3 as shown in SEQ ID NO: 17, or a CDRH3 sequence differing in 1 or 2 amino acids therefrom,
and/or a light chain comprising at least one CDR selected from the group consisting of
(d) a CDRL1 as shown in SEQ ID NO: 18, or a CDRL1 sequence differing in 1 or 2 amino acids therefrom,
(e) a CDRL2 as shown in SEQ ID NO: 19, or a CDRL2 sequence differing in 1 or 2 amino acids therefrom, and
(f) a CDRL3 as shown in SEQ ID NO: 20, or a CDRL3 sequence differing in 1 or 2 amino acids therefrom, or
an antibody recognizing the same epitope on the extracellular domain of FGFR4.

In another embodiment, the present invention refers to an antibody comprising a heavy chain amino acid sequence selected from the group consisting of SEQ ID NOs: 5 and 7 or at least the variable domain thereof or an amino acid sequence having an identity of at least 90% thereto and/or a light chain amino acid sequence selected from the group consisting of SEQ ID NOs: 6 and 8 or at least the variable domain thereof or an amino acid sequence having an identity of at least 90% thereto or to an antibody recognizing the same epitope on the extracellular domain of FGFR4.

In a particular preferred embodiment, the antibody is selected from the group consisting of 9A5 and 10F10 or an antibody recognizing the same epitope on the extracellular domain of FGFR4.

The antibody may be any antibody of natural and/or synthetic origin, e.g. an antibody of mammalian origin. Preferably, the constant domain—if present—is a human constant domain. The variable domain is preferably a mammalian variable domain, e.g. a humanized or a human variable domain. More preferably, the antibody is a chimeric, humanized or human antibody.

The antibody of the invention may be of the IgA-, IgD-, IgE, IgG- or IgM-type, preferably of the IgG- or IgM-type including, but not limited to, the IgG1-, IgG2-, IgG3-, IgG4-, IgM1- and IgM2-type. In most preferred embodiments, the antibody is of the human IgG1-, IgG2- or IgG4-type.

The term antibody includes "fragments" or "derivatives", which have at least one antigen binding site of the antibody. Antibody fragments include Fab fragments, Fab' fragments F(ab')$_2$ fragments as well as Fv fragments. Derivatives of the antibody include single chain antibodies, nanobodies, and diabodies. Derivatives of the antibody shall also include scaffold proteins having an antibody-like binding activity that bind to FGFR4.

Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Pluckthun, *Curr Opin Biotechnol*, 16, 459-69). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against FGFR4, either purified protein or protein displayed on the cell surface, for binding agents in an artificial scaffold library displayed in vitro, skills which are known in the art (Skerra, J. Mol. Recog., 2000; Binz and Plucktun, 2005). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. The inserted binding domains may include, for example, at least one CDR of an ant FGFR4 antibody, preferably at least one selected from the group of SEQ ID NOs: 9-20. Insertion can be accomplished by various methods known to those skilled in the art including, for example, polypeptide synthesis, nucleic acid synthesis of an encoding amino acid as well by various forms of recombinant methods well known to those skilled in the art.

As has been indicated above, the specificity of the antibody, antibody fragment, a derivative thereof lies in the amino acid sequence of the CDR. The variable domain (the heavy chain VH and light chain VL) of an antibody preferably comprises three complementary determining regions some-times called hypervariable regions, flanked by four relatively conserved framework regions or "FRs". Often, the specificity of an antibody is determined or largely determined by a CDR, such as a CDR of the VH chain or a plurality of CDRs. The person skilled in the art will readily appreciate that the variable domain of the antibody, antibody fragment or derivative thereof having the above-described CDRs can be used for the construction of antibodies of further improved specificity and biological function. Insofar, the present invention encompasses antibodies, antibody fragments or derivatives thereof comprising at least one CDR of the above-described variable domains and which advantageously have substantially the same, similar or improved binding properties as the antibody described in the appended examples. Starting from an antibody that comprises at least one CDR as recited in the attached sequence listing and required by the main embodiment of the invention, the skilled artisan can combine further CDRs from the originally identified monoclonal antibodies or different antibodies for an enhanced specificity and/or affinity. CDR grafting is well-known in the art and can also be used to fine-tune the specific affinity in other properties of the antibody, fragment or derivative thereof of the invention, as long as the original specificity is retained. It is advantageous that the antibody, fragment or derivative comprises at least two, more preferred at least three, even more preferred at least four such as at least five and particularly preferred all six CDRs of the original donor antibody. In further alternatives of the invention, CDRs from different originally identified monoclonal antibodies may be combined in a new antibody entity. In these cases, it is preferred that the three CDRs of the heavy chain originate from the same antibody whereas the three CDRs of the light chain all originate from a different (but all from the same) antibody. The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y.

The antibodies, antibody fragments or derivative thereof are optionally de-immunized for therapeutic purposes. The manufacture of de-immunized, e.g. humanized binding proteins may be carried out as described in U.S. Pat. Nos. 6,054,297, 5,886,152 and 5,877,293.

For therapeutic purposes, the antibody may be conjugated with a therapeutic effector group, e.g. a radioactive group or a cytotoxic group.

For diagnostic purposes, the antibody may be enzyme labelled. Suitable labels include radioactive labels, fluorescent labels, or enzyme labels.

The antibody of the invention has advantageous properties with respect to its binding specificity and/or biological activity. Preferably, the FGFR4 antibody exhibits at least one of the following characteristics:
High specificity for FGFR4, particularly human FGFR; antibodies do not significantly recognize other family members, e.g. FGFR1, FGFR2 and/or FGFR3;
Binding to an epitope on the extracellular domain;
Blocking or reducing of FGFR4 tyrosine phosphorylation;
Blocking or reducing of FGFR4 mediated signal transduction;
Decreasing or inhibiting cell growth;
Decreasing or inhibiting cell migration.

In a further preferred aspect, the antibody has a constant domain with effector functions, whereby FGFR4 expressing cells which have bound the antibody, antibody fragment or derivative thereof on the cell surface may be attacked by immune system functions. For example, the antibody may be capable of fixing complement and participating in complement-dependent cytotoxicity (CDC). Moreover, the antibody may be capable of binding to Fc receptors on effector cells, such as monocytes and natural killer (NK) cells, and participate in antibody-dependent cellular cytotoxicity (ADCC).

As mentioned above and in other words, the antibodies of the invention show advantageous properties with respect to their binding specificity and biological activity, in particular with respect to their capacity to recognize epitopes of the FGFR4, to decrease cell growth and cell migration, the ability to activate a further antineoplastic agent and/or sensitize tumor cells to a therapeutic treatment.

The antibodies of the invention may be obtained by a selection procedure wherein they are tested, e.g. by ELISA, FACS and Western Blot analysis for their cell binding properties, activities on either signal transduction pathways or cellular functions and selectivity between FGFR4 and the other FGFR family members. In a preferred embodiment the antibody specifically binds to/interacts with at least one epitope of the extracellular domain of a mammalian FGFR4, particularly a human FGFR4, and does not bind to/interact with other FGFR family members. The term "extracellular domain" relates to the portion of the FGFR4 extending into the extracellular environment. This domain comprises amino acids 1-360 of the human (?) FGFR4 molecule.

The present invention also encompasses antibodies that compete with the antibodies selected from the group comprising of 9A5 and 10F10 in binding the same epitope of the extracellular domain of the mammalian FGFR4.

To determine the epitope on FGFR4 recognized by the antibody, chemically prepared arrays of protein sequence derived short peptides derived from the amino acid sequence of the extracellular FGFR4 domain can be used to locate and identify antibody epitopes (Reinicke W., Methods Mol. Biol. 2004; 248:443-63). A further method to map the epitopes in the FGFR4 extracellular domain bound by the antibodies of the invention comprises Snaps/SELDI (Wang et al., Int J Cancer. 2001 Jun. 15; 92(6):871-6) or a routine cross-blocking assay such as that described in Antibodies, A Laboratory Manual, Cold Spring Harbor Laboratory, Ed Harlow and David Lane (1988), can be performed.

Affinity measurements of FGFR4 antibodies of the invention may be performed by indirect FACS Scatchard analysis. Preferably, this analysis comprises harvesting an appropriate number of cells of interest, washing with buffer and seeding on a plate. The cells may be centrifuged to remove supernatant and then resuspended with α-FGFR4 antibody or with antibody dilutions (e.g. 100 µl/well) starting with e.g. 20 µg/ml antibody, diluted e.g. in 1:2 dilution steps. Cell suspensions with antibody are incubated, washed with buffer and incubated with secondary antibody. The cell suspensions are incubated, washed with buffer and analyzed (FACS, Beckman Coulter). According to the FACS Scatchard analysis, the fluorescence mean is calculated for each measurement. Background staining (=without $1^{st}$ antibody) is subtracted from each fluorescence mean. Scatchard plot with x-value=fluorescence mean and y-value=fluorescence mean/concentration of antibody generated.

To select for antibodies which reduce ligand induced FGFR4 phosphorylation, cells can be preincubated with buffer (control) or antibody, then treated with ligand or control buffer. The cells are then lysed and the crude lysates can be centrifuged to remove insoluble material. Supernatants may be incubated with an antibody specific for FGFR4 and protein-A-sepharose to enable efficient precipitation. Following washing, the immunoprecipitates may be separated by SDS-PAGE. Western blots of the gels are then probed with anti-phosphotyrosine antibody. After visualization, the blots may be stripped and re-probed with an anti-FGFR4 antibody. Reflectance scanning densitometry of the gel can be performed in order to quantify the effect of the antibody in question on HRG-induced formation of the complex. Those antibodies which reduce of FGFR4 phosphorylation relative to control (untreated cells) are selected.

In vitro experiments can be conducted in order to determine the ability of the antibodies of the invention to inhibit ligand-stimulated cell proliferation. An appropriate number of cells of interests are incubated with antibody diluted in appropriate medium. Cells are stimulated by adding ligand directly to antibody solution and are then left to grow for 72 hr. AlamarBlue™ (BIOSOURCE) is added and incubated at 37° C. in the dark. Absorbance is measured at 590 nm every 30 min.

To select for those antibodies which reduce FGFR4 mediated cell migration, transmigration experiments can be performed. Serum-starved cells are incubated with antibody. An appropriate number of cells may be placed in the top chamber of coated transwells (BD Falcon, 8 μm pores). In the case of stimulation medium alone or containing a chemotactic agent is used in the bottom chamber. Cells are left to migrate and are subsequently stained. Stained nuclei are counted; percent inhibition is expressed as inhibition relative to a control antibody.

The effect of the antibody on ligand binding to FGFR4 can be determined by incubating cells which express this receptor (e.g. MDA-MB 453 breast cancer cells) with radiolabelled ligand (e.g. FGF1 or FGF19), in the absence (control) or presence of the FGFR4 antibody. Those antibodies which reduce the binding affinity of ligand for the FGFR4 receptor or which block binding of ligand to FGFR4 can be identified.

The anti-tumor efficacy of therapeutic antibodies may be evaluated in human xenograft tumor studies. In these studies, human tumors grow as xenografts in immunocompromised mice and therapeutic efficacy is measured by the degree of tumor growth inhibition. In order to determine, if the FGFR4 antibodies of the invention interfere with tumor growth of human cancer cells in nude mice, cells are implanted in nude/ nude mice. Tumors are subcutaneous, grown on the back of the animal. Treatment may be started immediately or when tumors reach a mean volume of 20-50 mm$^3$. Prior to first treatment, mice are randomized and statistical tests performed to assure uniformity in starting tumor volumes (mean, median and standard deviation) across treatment groups. Treatment is started with a loading dose of 50 mg/kg followed by 25 mg/kg injections once a week by intraperitoneal injection. A control arm receives a known antineoplastic agent, e.g. doxorubicin (pharmaceutical grade).

In a preferred embodiment of the invention, the antibody is a monoclonal antibody. Monoclonal antibodies can be prepared, for example, by the well-established techniques as originally described in Köhler and Milstein, Nature 256 (1975), 495, and Galfre, Meth. Enzymol. 73 (1981), 3, which comprise the fusion of rat myeloma cells to spleen cells derived from immunized mammals with modifications developed by the art.

In an additionally preferred embodiment of the invention, the antibody may be a Fab-fragment, a F(ab$_2$)'-fragment, a single-chain antibody, a chimeric antibody, a CDR-grafted antibody, a bivalent antibody-construct, a humanized antibody, a human, a synthetic antibody, or a chemically modified derivative thereof, a multispecific antibody, a diabody, a nanobody, a Fv-fragment, or another type of a recombinant antibody Fragments or derivatives of the above antibodies directed to the aforementioned epitopes can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of FGFR4 (Schier, Human Antibodies Hybridomas 7 (1996), 97-105; Malmborg, J. Immunol. Methods 183 (1995), 7-13).

The antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). The production of chimeric antibodies is described, for example, in WO 89/09622.

Humanized forms of the antibodies may be generated according to the methods known in the art such as chimerization or CDR grafting. Methods for the production of humanized antibodies are well known in the art and are described in, e.g., EP-A1 0 239 400 and W090/07861. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A de-immunized antibody is a protein devoid of or reduced for epitopes that can be recognized by T helper lymphozytes. An example how to identify said epitopes is shown in Tangri et al., (J Immunol. 2005 Mar. 15; 174(6): 3187-96.).

Further antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735.

As discussed above, the antibody of the invention may exist in a variety of forms besides complete antibodies; including, for example, Fv, Fab and F(ab)$_2$ as well as in single chains; see e.g. W088/09344.

If desired, the antibodies of the invention may be mutated in the variable domains of the heavy and/or light chains to alter a binding property of the antibody. For example, a mutation may be made in one or more of the CDR regions to increase or decrease the Kd of the antibody for FGFR4, or to alter the binding specificity of the antibody. Techniques in site directed mutagenesis are well-known in the art. See, e.g., Sambrook et al. and Ausubel et al., supra. Furthermore, mutations may be made at an amino acid residue that is known to be changed compared to germline in a variable region of an FGFR4 antibody. In another aspect, mutations may be introduced into one or more of the framework regions. A mutation may be made in a framework region or constant domain to increase the half-life of the FGFR4 antibody. See, e.g., WO 00/09560. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

The invention further relates to a nucleic acid molecule encoding the antibody, antibody fragment or derivative thereof of the invention. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions. In a particular preferred embodiment of the present invention, the nucleic acid molecule is a cDNA molecule.

Preferably, the invention relates to an isolated nucleic acid molecule selected from the group consisting of:
(a) a nucleic acid sequence encoding a polypeptide of SEQ ID NOs: 5-20,
(b) a nucleic acid sequence as shown in SEQ ID NOs: 1-4,
(c) a nucleic acid complementary to any of the sequences in (a) or (b); and
(d) a nucleic acid sequence capable of hybridizing to (a), (b) or (c) under stringent conditions.

The term "hybridizing under stringent conditions" means that two nucleic acid fragments hybridize with one another under standardized hybridization conditions as described for example in Sambrook et al., "Expression of cloned genes in E. coli" in Molecular Cloning: A laboratory manual (1989), Cold Spring Harbor Laboratory Press, New York, USA. Such conditions are for example hybridization in 6.0×SSC at about 45° C. followed by a washing step with 2.0×SSC at 50° C., preferably 2.0×SSC at 65° C., or 0.2×SSC at 50° C., preferably 0.2×SSC at 65° C.

The invention also relates to a vector comprising a nucleic acid molecule of the invention. Said vector may be, for example, a phage, plasmid, viral or retroviral vector. Retroviral vectors may be replication competent or replication defective. In the latter case, viral propagation generally will occur only in complementing host/cells.

The nucleic acid molecules of the invention may be joined to a vector containing selectable markers for propagation in a host. Generally, a plasmid vector is introduced in a precipitate such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

Preferably, the vector of the invention is an expression vector wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in E. coli, and examples for regulatory elements permitting expression in eukaryotic host cells are the AOXI or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogen) or pSPORTI (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001, Third Edition) N.Y. and Ausubel, Current Protocols in Molecular Biology, Green Publishing Associates and Wiley Interscience, N.Y. (1994). Alternatively, the nucleic acid molecules of the invention can be reconstituted into liposomes for delivery to target cells.

The invention further relates to a host comprising the vector of the invention. Said host may be a prokaryotic or eukaryotic cell or a non-human transgenic animal. The polynucleotide or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host can be any prokaryotic or eukaryotic cell, such as a bacterial, insect, fungal, plant, animal, mammalian or, preferably, human cell. Preferred fungal cells are, for example, those of the genus Saccharomyces, in particular those of the species S. cerevisiae. The term "prokaryotic" is meant to include all bacteria which can be transformed or transfected with a polynucleotide for the expression of a variant polypeptide of the invention. Prokaryotic hosts may include gram negative as well as gram positive bacteria such as, for example, E. coli, S. typhimurium, Serratia marcescens and

*Bacillus subtilis*. A polynucleotide coding for a mutant form of variant polypeptides of the invention can be used to transform or transfect the host using any of the techniques commonly known to those of ordinary skill in the art. Methods for preparing fused, operably linked genes and expressing them in bacteria or animal cells are well-known in the art (Sambrook, Molecular Cloning A Laboratory Manual, Cold Spring Harbor Laboratory (2001, Third Edition). The genetic constructs and methods described therein can be utilized for expression of variant antibodies, antibody fragments or derivatives thereof of the invention in, e.g., prokaryotic hosts. In general, expression vectors containing promoter sequences which facilitate the efficient transcription of the inserted nucleic acid molecule are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the grown medium, cellular lysates, or cellular membrane fractions. The isolation and purification of the microbially or otherwise expressed antibodies, antibody fragments or derivatives thereof of the invention may be by any conventional means such as, for example, preparative chromatographic separations and immunological separations such as those involving the use of monoclonal or polyclonal antibodies.

In a preferred embodiment of the invention, the host is a bacterium, fungal, plant, amphibian or animal cell. Preferred animal cells include but are not limited to Chinese hamster ovary (CHO) cells, baby hamster kidney (BHK) cells, monkey kidney cells (COS), 3T3 cells, NSO cells and a number of other cell lines, including human cells. In another preferred embodiment, said animal cell is an insect cell. Preferred insect cells include but are not limited to cells of the SF9 cell lines In a more preferred embodiment of the invention, said host is a human cell or human cell line. Said human cells include, but are not limited to Human embryonic kidney cells (HEK293, 293T, 293 freestyle). Furthermore, said human cell lines include, but are not limited to HeLa cells, human hepatocellular carcinoma cells (e.g., Hep G2), A549 cells.

The invention also provides transgenic non-human animals comprising one or more nucleic acid molecules of the invention that may be used to produce antibodies of the invention. Antibodies can be produced in and recovered from tissue or body fluids, such as milk, blood or urine, of goats, cows, horses, pigs, rats, mice, rabbits, hamsters or other mammals. See, e.g., U.S. Pat. Nos. 5,827,690; 5,756,687; 5,750,172; and 5,741,957. As described above, non-human transgenic animals that comprise human immunoglobulin loci can be produced by immunizing with FGFR4 or a portion thereof.

The invention additionally relates to a method for the preparation of an antibody, comprising culturing the host of the invention under conditions that allow synthesis of said antibody and recovering said antibody from said culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982).

The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention.

It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

In a preferred embodiment of the present invention, the antibody is coupled to an effector, such as a radioisotope or a toxic chemotherapeutic agent. Preferably, these antibody conjugates are useful in targeting cells, e.g. cancer cells, expressing FGFR4, for elimination. The linking of antibodies/antibody fragments of the invention to radioisotopes e.g. provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. Preferred radioisotopes include e.g. $^{3}H$, $^{14}C$, $^{15}N$, $^{35}S$, $^{90}Y$, $^{99}Tc$, $^{111}In$, $^{125}I$, $^{131}I$.

Furthermore, the antibodies of the invention can be used to treat cancer when being conjugated with toxic chemotherapeutic drugs such as geldanamycin (Mandler et al., *J. Natl. Cancer Inst.*, 92(19), 1549-51 (2000)) and maytansin, for example, the maytansinoid drug, DM1 (Liu et al., *Proc. Natl. Acad. Sci. U.S.A.* 93:8618-8623 (1996) and auristatin-E or monomethylauristatin-E (Doronina et al., *Nat. Biotechnol.* 21:778-784 (2003) or calicheamicin. Different linkers that release the drugs under acidic or reducing conditions or upon exposure to specific proteases are employed with this technology. The antibodies of the invention may be conjugated as described in the art.

The invention further relates to a pharmaceutical composition comprising the antibody, the nucleic acid molecule, the vector, the host of the invention or an antibody obtained by the method of the invention.

The term "composition" as employed herein comprises at least one compound of the invention. Preferably, such a composition is a pharmaceutical or a diagnostic composition.

It is preferred that said pharmaceutical composition comprises a pharmaceutically acceptable carrier and/or diluent. The herein disclosed pharmaceutical composition may be partially useful for the treatment of disorders associated with, accompanied by or caused by EGFR4 expression, overexpression or hyperactivity, e.g. hyperproliferative diseases, inflammatory diseases or metabolic diseases. Said disorders comprise, but are not limited to psoriasis, obesity, cancer, e.g. breast, lung, colon, kidney, lymphoma, skin, ovary, prostate, pancreas, esophagus, barret, stomach, bladder, cervix, liver, thyroid cancer, melanoma, or other hyperplastic or neoplastic diseases or other FGFR4 expressing or overexpressing diseases.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 µg and 100 mg/kg body weight per dose; however, doses below or above this exemplary range are envisioned, especially considering the aforementioned factors. If the regimen is a continuous infusion, it should also be in the range of 1 pg to 100 mg per kilogram of body weight per minute.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. It is particularly preferred that the pharmaceutical composition comprises further active agents like, e.g. an additional anti-neoplastic agent, small molecule inhibitor, anti-tumor agent or chemotherapeutic agent.

The invention also relates to a pharmaceutical composition comprising the antibody of the invention in combination with at least one further anti-neoplastic agent. Said combination is effective, for example, in inhibiting abnormal cell growth.

Many antineoplastic agents are presently known in the art. In one embodiment, the antineoplastic agent is selected from the group of therapeutic proteins including but not limited to antibodies or immunomodulatory proteins. In another embodiment the antineoplastic agent is selected from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and antiangiogenesis agents.

In yet another embodiment the pharmaceutical composition comprises the antibody and a an inhibitor of a member of the EGFR family, e.g. an EGFR, HER2, HER3 or HER4 inhibitor, particularly a HER2 inhibitor, e.g. an antagonistic antibody or a small molecule inhibitor.

The pharmaceutical composition of the invention can be used in human medicine and can be used also for veterinary purposes.

Additionally, the invention relates to the use of the antibody of the invention, the nucleic acid molecule, the vector, the host of the invention or an antibody obtained by the method of the invention for the preparation of a pharmaceutical composition for diagnosis, prevention or treatment of hyperproliferative diseases, inflammatory diseases or metabolic diseases, particularly of disorders associated with, accompanied by or caused by FGFR4 expression, overexpression or hyperactivity.

A hyperproliferative disease as mentioned above includes any neoplasia, i.e. any abnormal and/or uncontrolled new growth of tissue. The term "uncontrolled new growth of tissue" as used herein may depend upon a dysfunction and/or loss of growth regulation. A hyperproliferative disease includes tumor diseases and/or cancer, such as metastatic or invasive cancers.

In a preferred embodiment of the use of the invention, said hyperproliferative disease is in particular breast, lung, colon, kidney, lymphoma, skin, ovary, prostate, pancreas, esophagus, barret, stomach, bladder, cervix, liver, thyroid cancer, melanoma, hyperplastic or neoplastic diseases or other FGFR4 expressing or overexpressing hyperproliferative diseases.

In yet another embodiment the present invention relates to a diagnostic composition comprising the antibody of the invention, the nucleic acid molecule, the vector, the host of the invention or an antibody obtained by the method of the invention and optionally a pharmaceutically acceptable carrier.

The diagnostic composition of the invention is useful in the detection of an undesired expression, overexpression or hyperactivity of the mammalian FGFR4 in different cells, tissues or another suitable sample, comprising contacting a sample with an antibody of the invention, and detecting the presence of FGFR4 in the sample. Accordingly, the diagnostic composition of the invention may be used for assessing the onset or the disease status of a hyperproliferative disease.

Furthermore, malignant cells, such as cancer cells expressing FGFR4, can be targeted with the antibody of the invention. The cells which have bound the antibody of the invention might thus be attacked by immune system functions such as the complement system or by cell-mediated cytotoxicity, therefore reducing in number of or eradicating cancer cells. These considerations equally apply to the treatment of metastases and re-current tumors.

In another aspect of the present invention, the antibody of the invention is coupled to a labelling group. Such antibodies are particularly suitable for diagnostic applications. As used herein, the term "labelling group" refers to a detectable marker, e.g. a radiolabelled amino acid or biotinyl moieties that can be detected by marked avidin. Various methods for labelling polypeptides and glycoproteins, such as antibodies, are known in the art and may be used in performing the present invention. Examples of suitable labelling groups include, but are not limited to, the following: radioisotopes or radionuclides (e.g. $^{3}H$, $^{14}C$, $^{15}N$, $^{35}S$, $^{90}Y$, $^{99}Tc$, $^{111}In$, $^{125}I$, $^{131}I$), fluorescent groups (e.g. FITC, rhodamine, lanthanide phosphors), enzymatic groups (e.g. horseradish peroxidase, β-galactosidase, luciferase, alkaline phosphatase), chemiluminescent groups, biotinyl groups, or predetermined polypeptide epitopes recognized by a secondary reporter (e.g.

leucine zipper pair sequences, binding sites for secondary antibodies, metal binding domains, epitope tags).

In certain aspects, it may be desirable, that the labelling groups are attached by spacer arms of various lengths to reduce potential steric hindrance.

The above embodiment of the invention is particularly important. Since the antibodies of the invention show a broad scope of applicability with respect to different mammalian species that can be treated, the diagnostic composition of the invention is also useful and applicable in different mammalian species.

In another embodiment the present invention relates to a method of assessing for the presence of FGFR4 expressing cells comprising contacting the antibody of the invention with cells or a tissue suspected of carrying FGFR4 on their/its surface. Suitable methods for detection of FGFR4 expression in a sample may be an Enzyme-Linked Immunosorbent Assay (ELISA) or Immunohistochemistry (IHC).

An ELISA assay may be carried out in a microtiter plate format, wherein e.g. wells of a microtiter plate, are adsorbed with a FGFR4 antibody. The wells are rinsed and treated with a blocking agent such as milk protein or albumin to prevent nonspecific adsorption of the analyte. Subsequently the wells are treated with a test sample. After rinsing away the test sample or standard, the wells are treated with a second FGFR4 antibody that is labelled, e.g. by conjugation with biotin. After washing away excess secondary antibody, the label is detected, e.g. with avidin-conjugated horseradish peroxidase (HRP) and a suitable chromogenic substrate. The concentration of the FGFR4 antigen in the test samples is determined by comparison with a standard curve developed from standard samples.

For IHC, paraffin-embedded tissues may be used, wherein the tissues are, e.g. first deparaffinized in xylene and then dehydrated, e.g. with ethanol and rinsed in distilled water. Antigenic epitopes masked by formalin-fixation and paraffin-embedding may be exposed by epitope unmasking, enzymatic digestion or saponin. For epitope unmasking paraffin sections may be heated in a steamer, water bath or microwave oven for 20-40 min in a epitope retrieval solution as for example 2N HCl solution (pH 1.0). In the case of an enzyme digestion, tissue sections may be incubated at 37° C. for 10-30 minutes in different enzyme solutions such as proteinase K, trypsin, pronase, pepsin etc.

After rinsing away the epitope retrieval solution or excess enzyme, tissue sections are treated with a blocking buffer to prevent unspecific interactions. The primary FGFR4 antibody is added at appropriate concentrations. Excess primary antibody is rinsed away and sections are incubated in peroxidase blocking solution for 10 min at room temperature. After another washing step, tissue sections are incubated with a secondary labelled antibody, e.g. labelled with a group that might serve as an anchor for an enzyme. Examples therefore are biotin labelled secondary antibodies that are recognized by streptavidin coupled horseradish peroxidase. Detection of the antibody/enzyme complex is achieved by incubating with a suitable chromogenic substrate.

In an additional embodiment the present invention relates to a method of blocking FGFR4 function comprising contacting the antibody of the invention with cells or a tissue suspected of carrying FGFR4 on their/its surface under conditions, wherein the antibody is capable of blocking FGFR4 function. The contacting may be in vitro or in vivo.

The invention also relates to a method of treating a hyperproliferative disease, a metabolic disease or an inflammatory disease comprising administering to a patient in need thereof a suitable dose of the antibody or antibody fragment or derivative thereof of the present invention. The hyperproliferative disease is preferably selected from disorders associated with, accompanied by or caused by EGFR4 expression, overexpression or hyperactivity, such as cancer, e.g. breast, lung, colon, kidney, lymphoma, skin, ovary, prostate, pancreas, esophagus, barret, stomach, bladder, cervix, liver, thyroid cancer and hyperplastic and neoplastic diseases or other FGFR4 expressing or overexpressing hyperproliferative diseases.

The invention further relates to a method of treating a disease wherein the antibody of the invention is administered to a mammal and wherein said disease is correlated directly or indirectly with the abnormal level of expression or activity of FGFR4.

Finally, the invention relates to a kit comprising the antibody, antibody fragment or derivative thereof of the invention, the nucleic acid molecule encoding said components and/or the vector of the invention.

All embodiments covering the compounds disclosed herein can be used as single compounds or in combination for the preparation of a medicament.

FIGURE LEGENDS

FIG. 1. Anti-FGFR4 antibodies 10F10 and 9A5 do not bind to the other members of the family, FGFR1-3. Extracellular domains of FGFR1-4 were expressed as myc-tagged recombinant proteins. Antibody binding to recombinant proteins or BSA was detected by ELISA, using an anti-myc antibody to control for equivalent coating.

Figure 2:
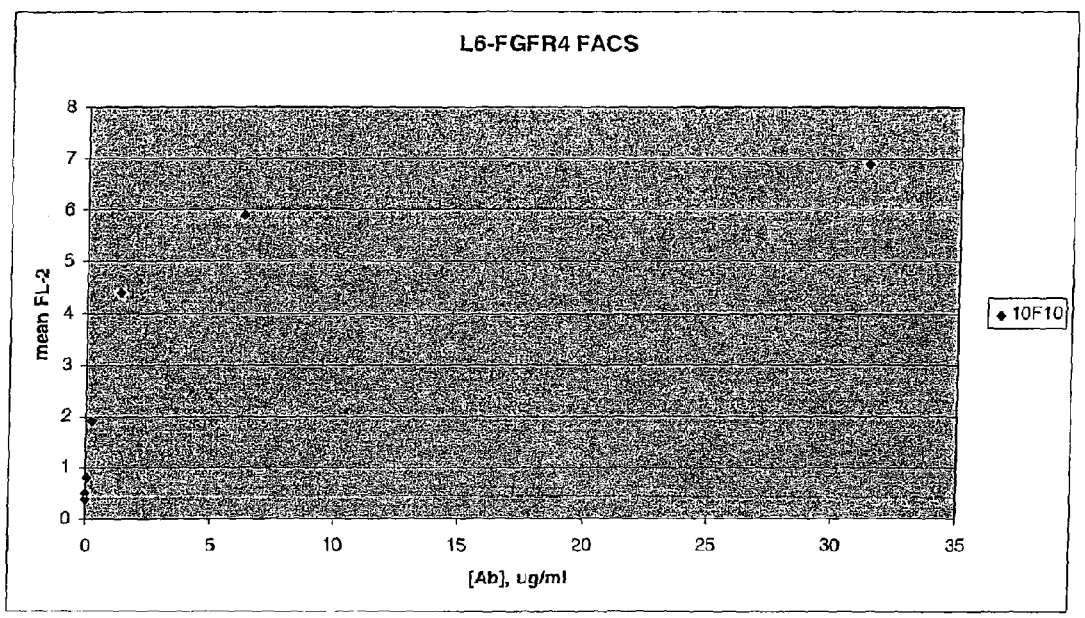

FIG. 2. Determination of 10F10 antibody affinities in FACS Scatchard experiments on L6-FGFR4 cells.

Figure 3:
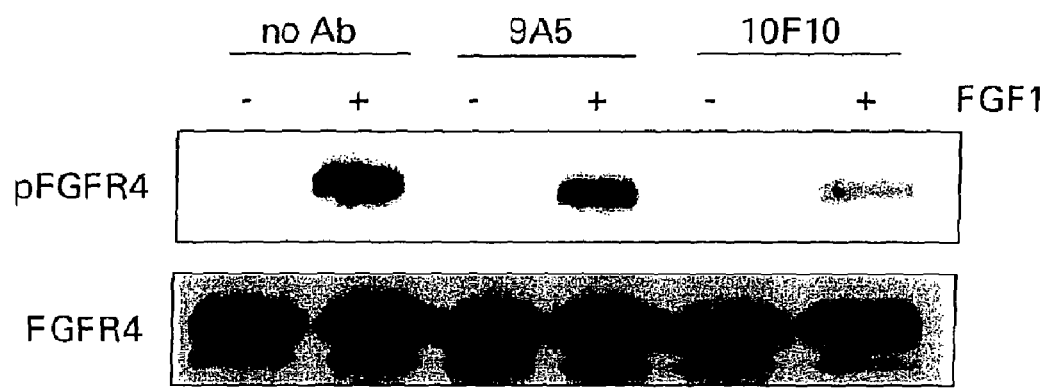

FIG. 3. Anti-FGFR4 antibodies 10F10 and 9A5 inhibit FGF1-induced FGFR4 tyrosine phosphorylation. L6-FGFR4 cells were starved, incubated with antibodies for 1 hour and stimulated with 10 ng FGF1 for 10 minutes. FGFR4 was precipitated from cell lysates with antibody C-19 and the Western blot probed with anti-phospho-tyrosine antibody 4G10 and re-probed with C-19.

Figure 4:
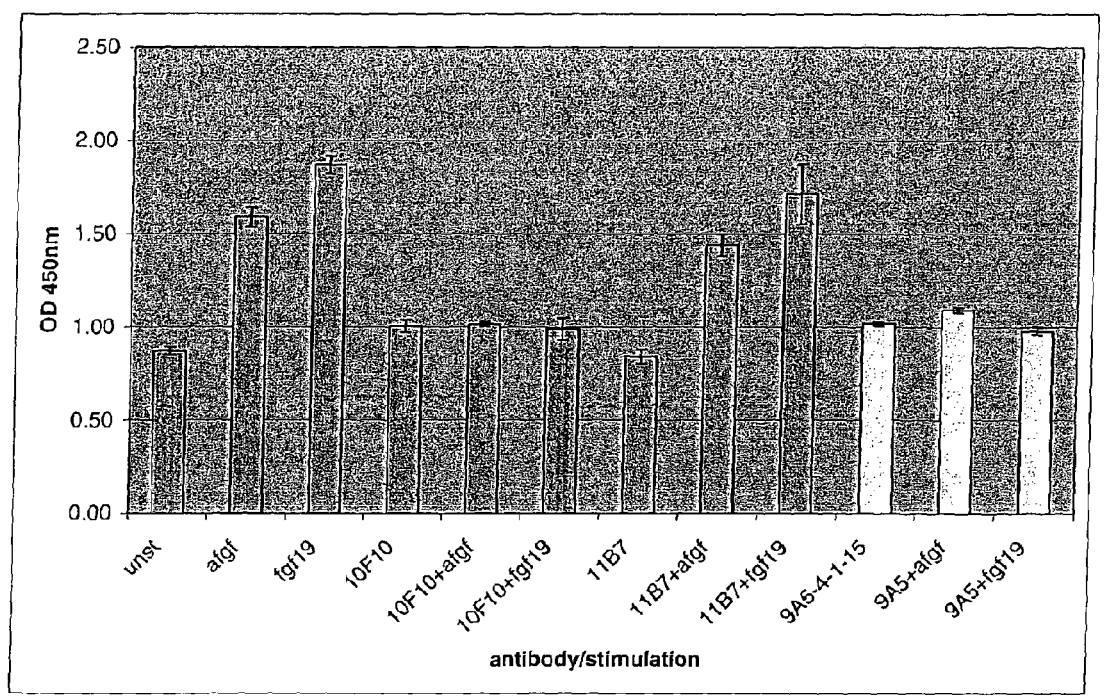

FIG. 4. Anti-FGFR4 antibodies 10F10 and 9A5 inhibit Erk phosphorylation stimulated by FGF1 or FGF19 in FGFR4-transfected L6 myoblasts. L6 cells stably transfected with FGFR4 were starved, incubated with FGFR4 antibodies 10F10 or 9A5 or control antibody 11B7 and stimulated with FGF1 or FGF19. Erk phosphorylation was determined in a cell ELISA as described in example 2.

Figure 5:
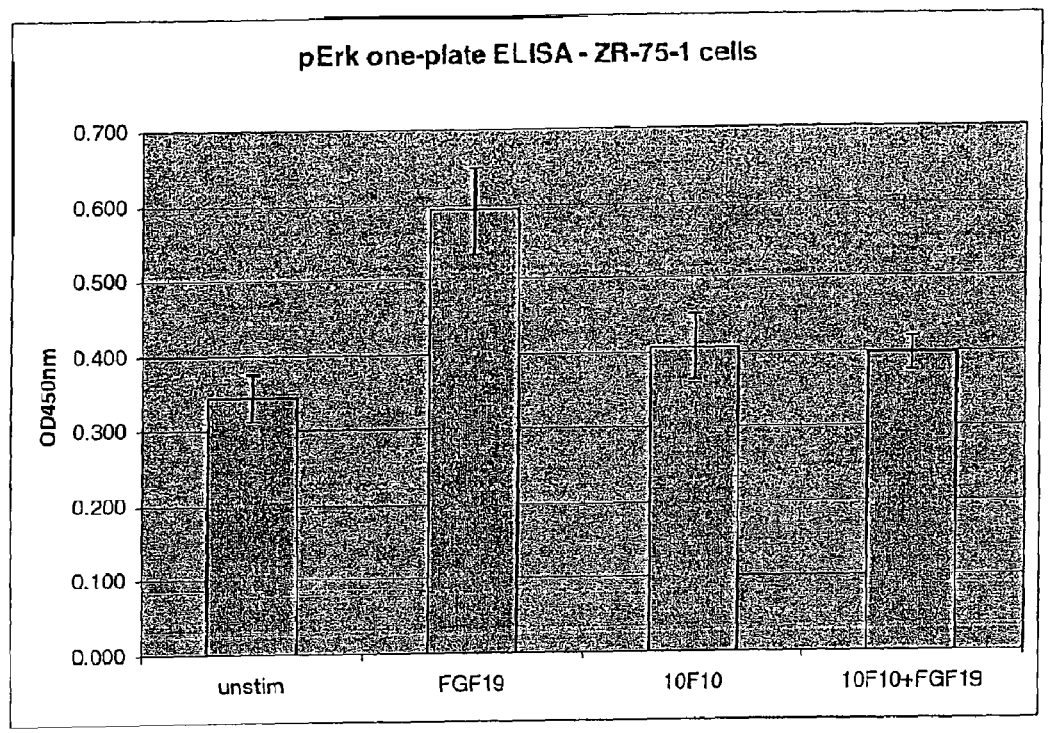

FIG. 5. Antibody 10F10 inhibits Erk phosphorylation stimulated by FGF19 in ZR-75-1 breast cancer cells. Experimental condition were similar to those in FIG. 2.

EXAMPLES

Example 1

Generation of the Antibodies

For generation of antibodies that bind specifically to FGFR4 a recombinant Glutathione-S-Transferase (GST) (Smith & Johnson, 1988) fusion protein comprising the human FGFR-4 extracellular domain (FGFR-4 ex) was prepared. We used the cloning vector pSj26(mod) (Seiffert et al., 1999) that was designed for the eukaryotic expression and secretion of recombinant fusion proteins and was derived from the pcDNA3 cloning vector (Invitrogen, Groningen, The Netherlands) by inserting the complete DNA sequence coding for *Schistosoma japonicum* glutathione-S-transferase (GST) (Pharmacia Biotech, Freiburg, Germany) in the XhoI and ApaI sites of pcDNA3.

The extracellular domain of human FGFR-4 was PCR amplified using the following primers:

```
sense:
                                        (SEQ ID NO: 21)
5'-GAATTCGCCACCATGCGGCTGCTGCTGGCCCTGTTG-3', antisense:
                                        (SEQ ID NO: 22)
5'-CGAGGCCAGGTATACGGACATCATCCTCGAGTT-3'.
```

The PCR product was digested with EcoRI and XhoI and cloned into pSj26(mod). The resulting pSj26(mod)-FGFR-4ex expression plasmid was transfected into 293 cells (ATCC CRL-1573) by the calcium phosphate DNA coprecipitation method. Cells were grown in Dulbecco's modified Eagle's medium (DMEM) supplemented with 10% FCS. After selection with 1 mg/ml G418 (Sigma, Deisenhofen, Germany) for two weeks, surviving clones were tested for expression and secretion of the fusion protein by Western blot analysis with antibodies against GST. High-expressing cells were used to produce FGFR-4ex. Medium was collected from confluent cultures every two days. One liter of collected medium was sterile filtered and incubated with 1 ml glutathione Sepharose (Pharmacia Biotech, Freiburg, Germany) overnight at 4° C. The Sepharose was separated and washed with phosphate-buffered saline (PBS). Elution was performed with 5 ml 10 mmol/l glutathione at 20° C. Eluted fusion protein was dialyzed $1:10^6$ (vol/vol) in PBS/10% glycerol. Protein concentration was determined using MicroBCA protein determination kit (Pierce, Rockford, Ill.).

Monoclonal antibodies were raised by injection of approximately 50 µg of FGFR4-ECD-GST fusion protein both i.p. and subcutaneously into Lou/C or Long Evans rats using CPG2006 (TIB MOLBIOL) or Freund's incomplete adjuvant as adjuvants. After an 8-week interval, a final boost was given i.p and subcutaneously 3 d before fusion. Fusion of the myeloma cell line P3X63-Ag8.653 with the rat immune spleen cells was performed according to standard procedures. Hybridoma supernatants were analyzed for isotype and subclass by ELISA and tested by FACS for binding to CHO-FGFR4 cells.

A determination of nucleotide sequences encoding antibodies as generated above, was carried out. SEQ ID NO:1 and 2 show a nucleotide sequence of the heavy or light chain regions of the antibody 10F10. SEQ ID NO: 3 and 4 show the nucleotide sequence of the heavy or light chain variable regions of the antibody 9A5. The amino acid sequences of the respective heavy and light chain regions are shown in SEQ ID NO: 5-8.

SEQ ID NO: 9-14 show the amino acid sequences HCDR1, HCDR2, HCDR3, LCDR1, LCDR2 and LCDR3 of antibody 10F10. SEQ ID NO:15-20 show the amino acid sequences HCDR1, HCDR2, HCDR3, LCDR1, LCDR2 and LCDR3 of antibody 9A5.

Example 2

Anti-FGFR4 Antibodies 10F10 and 9A5 do not Bind to the Other Members of the Family, FGFR1-3

Recombinant FGFR1-4 ECDs or BSA were coated to Maxisorp plates (Nunc, x) at 12.5 nM (100 µl per well) at 4° C. over night. After one wash with washing buffer (PBS pH 7.4, 0.05% Tween-20), plates were blocked with 1% BSA in washing buffer (blocking buffer) for 2 hours at room temperature. FGFR4 antibodies 10F10 and 9A5 as described in Example 1, non-binding control antibody 13F2 or anti-myc antibody 9E10 (Abcam) were added at 1 µg/ml in blocking buffer (100 µl per well) and incubated for 2 hours at room temperature. Plates were washed 6 times with washing buffer and incubated with the appropriate, POD-coupled secondary antibodies for 45 minutes at room temperature. After 6 washes with washing buffer and one wash with PBS, POD activity was determined by incubation with 100 µl TMB POD substrate (Calbiochem) per well for 5 minutes at room temperature followed by addition of stop solution (250 mM HCl, 100 ml). Absorbance was quantified in an ELISA reader at 450 nm (FIG. 1).

Example 3

Generation of Cells Overexpressing FGFR4

Appropriate FGFR-4 cDNAs were amplified from K562 cells (ATCC CCL-243), and subcloned into the Bluescript I KS vector (Stratagene) according to standard protocols (Current Protocols). The FGFR4 cDNA was then cloned into the pLXSN vector (Stratagene). The packaging cell line GF+E 86 (Markowitz et al., 1988) that produces ecotrophic viruses was transfected with this vector using calcium phosphate DNA coprecipitation. The supernatant of transfected GF+E 86 cells was collected and filtered through a 0.45 µm filter. Cells infected with the vector pLXSN alone were used as controls. For infection of rat L6 myoblasts, which does not express detectable amounts of FGFR-4, cells were incubated with viral supernatant for 24 h. After 48 h, medium was replaced with medium containing 400 µg/ml G418 and further selected under G418 for 14 days.

Accordingly, CHO cells expressing FGFR4 were generated by transfection of parental CHO cells with FGFR4 cDNA cloned into the pcDNA3 vector. Clonal cells lines were generated by limited dilution. FGFR-4 expression was determined by western blot analysis.

Example 4

Determination of 10F10 and 9A5 Antibody Affinities in FACS Scatchard Experiments on L6-FGFR4 Cells L6-FGFR4 cells were harvested by incubation with 10 mM EDTA in PBS and resuspended at 6 million cells per ml in FACS buffer (PBS pH 7.4, 3% FCS, 0.1% NaN$_3$). In a round-bottom microtiter plate, 100 µl of cell suspension were added to 100 µl of antibody solution containing antibodies 10F10 or 9A5 at concentrations between 31.25 and 0.01 µg/ml in FACS buffer. Antibody binding was allowed to proceed for 2 hours ice. Then, cells were washed twice with 250 µl FACS buffer per well, and resuspended in 200 µl of secondary antibody (anti-rat-PE; Jackson), diluted 1:50 in FACS buffer. After 45 minutes of incubation, cells were again washed twice in FACS buffer, then resuspended in 500 ml of PBS for FACS analysis. Analysis was carried out on a Beckman-Coulter FACS. To determine the apparent affinity constant $K_{Dapp}$, mean fluorescence values were plotted against the ratio of mean fluorescence and the corresponding antibody contration ([M]). The calculated $K_{Dapp}$ resulted from the inverse slope of the straight line (FIG. 2).

Example 5

Anti-FGFR4 Antibodies 10F10 and 9A5 Inhibit FGF1-Induced FGFR4 Tyrosine Phosphorylation $1.5 \times 10^6$ L6-FGFR4 cells were seeded in a 10-cm culture dishes and the following day starved for 24 hours in serum-free medium. Then, cells were incubated with antibodies 10F10 or 9A5 at 10 µg/ml for 1 hour and stimulated with 10 ng/ml FGF1 (R&D Systems, x) for 10 minutes. Cells were scraped off in 1 ml lysis buffer (50 mM Tris-HCl, pH 7.4, 1% Triton-X-100, 150 mM NaCl, 1 mM EDTA, 1 mM PMSF, aprotinin/leupeptin, pepstatin 1 µg/ml each, 1 mM $Na_3VO_4$, 1 mM NaF) on ice and centrifuged for 10 minutes at 10,000×g, 4° C. 1 ml of the supernatant were incubated with 20 µl of a suspension of protein A-sepharose beads and 1 µg of the polyclonal anti-FGFR4 antibody C16 (Santa Cruz) on a rotator wheel at 4° C. over night. The beads were washed three times with HNTG buffer (20 mM HEPES pH 7.5, 150 mM NaCl, 0.1% Triton-X-100, 10% glycerol) and boiled in 40 µl Laemmli buffer. After SDS PAGE, proteins were blotted onto a nitrocellulose membrane, which was subsequently blocked and incubated over night with anti-phospho-tyrosine antibody 4G10 (Upstate). After 3 washes, the membrane was incubated in HRP-coupled secondary antibody for 2 hours at room temperature and washed gain 3 times. Detection was done using the ECL system (GE Healthcare) (FIG. 3).

Example 6

Anti-FGFR4 Antibodies 10F10 and 9A5 Inhibit Erk Phosphorylation Stimulated by FGF1 or FGF19 in FGFR4-Transfected L6 Myoblasts L6-FGFR4 cells were seeded into a 96-well plate at a density of 10,000 cells per well in DMEM/10% FCS. Cells were starved for 24 hours in serum-free medium, then antibodies 10F10, 9A5 or I11B7 were added at 10 µg/ml in fresh, serum-free medium. After 1 hour of incubation, cells were stimulated by addition of 10 ng/ml FGF1 or 600 ng/ml FGF19; FGF19 had been purified by StrepTactin-affinity chromatography (IBA) after expression from HEK-293 cells as Strep-tagged recombinant protein. For construction of the expression construct, the coding sequence of FGF19 had been inserted into the vector pcDNA3, and HEK-293 had been stably transfected using Lipofectamine 2000 (Invitrogen) and selection with 500 µg/ml G418.

After stimulation, cells were fixed by addition of 4% formaldehyde in PBS and incubation for 1 hour at room temperature. After 2 times washing with washing buffer (PBS pH 7.4, 0.1% Tween 20) for 5 minutes each, the plate was incubated with 100 µl of quenching buffer (1% $H_2O_2$ and 0.1% $NaN_3$ in washing buffer) per well. After two more washes, 100 µl of blocking buffer (PBS, 0.5% BSA) were added per well and the plate incubated at 4° C. over night. The next day, anti-phosphoErk antibody (Cell Signaling Technologies) was added at a dilution of 1:3000 in dilution buffer (PBS, 0.5% BSA, 0.05% Tween-20, 5 mM EDTA) and incubated for 4 hours at room temperature. Cells were washed 3 times with 200 µl washing buffer per well and incubated with POD-conjugated secondary antibody for 90 minutes at room temperature. After 3 washes with washing buffer and one with PBS, 100 µl of TMB were added and the plate incubated for 20 minutes at room temperature. The absorbance at 450 nm was measured after addition of 100 µl of stop solution per well in an ELISA reader (FIG. 4).

Example 7

Antibody 10F10 Inhibits Erk Phosphorylation Stimulated by FGF19 in ZR-75-1 Breast Cancer Cells ZR-75-1 cells were obtained from ATCC and routinely culture in RPMI/10% FCS. The experimental conditions for antibody incubation, stimulation and PhosphoErk-ELISA were identical to those described in Example 6. It was found that antibody 10F10 is capable of blocking FGF19 stimulated Erk phosphorylation. (FIG. 5).

LITERATURE

Bange, J., D. Prechtl, Y. Cheburkin, K. Specht, N. Harbeck, M. Schmitt, T. Knyazeva, S. Muller, S. Gartner, I. Sures, H. Wang, E. Imyanitov, H. U. Haring, P. Knayzev, S. Iacobelli, H. Hofler, and A. Ullrich. 2002. Cancer progression and tumor cell motility are associated with the FGFR4 Arg (388) allele. *Cancer Res JID*-2984705R 62:840-847.

Binz H K, Pluckthun A. Engineered proteins as specific binding reagents. Curr Opin Biotechnol. 2005 August; 16(4): 459-69.

Eswarakumar, V. P., I. Lax, and J. Schlessinger. 2005. Cellular signaling by fibroblast growth factor receptors. *Cytokine Growth Factor Rev.* 16:139-149.

Cavallaro, U., J. Niedermeyer, M. Fuxa, and G. Christofori. 2001. N-CAM modulates tumour-cell adhesion to matrix by inducing FGF-receptor signalling. *Nat. Cell Biol.* 3:650-657.

Gao, G. and M. Goldfarb. 1995. Heparin can activate a receptor tyrosine kinase. *EMBO J.* 14:2183-2190.

Jaakkola S, Salmikangas P, Nylund S, Partanen J, Armstrong E, Pyrhonen S, Lehtovirta P, Nevanlinna H. Amplification of fgfr4 gene in human breast and gynecological cancers. Int J Cancer. 1993 May 28; 54(3):378-82.

Klint P, Claesson-Welsh L. Signal transduction by fibroblast growth factor receptors. Front Biosci. 1999 Feb. 15; 4:D165-77.

Leung H Y, Gullick W J, Lemoine N R. Expression and functional activity of fibroblast growth factors and their receptors in human pancreatic cancer. Int J Cancer. 1994 Dec. 1; 59(5):667-75.

McKeehan W L, Kan M, Mol Reprod Dev. 1994 September; 39(1):69-81.

McKeehan W L, Wang F, Kan M. The heparan-sulfate fibroblast growth-factor family: diversity of structure and function. Prog Nucleic Acid Res Mol. Biol. 1998; 59:135-176.

Morimoto, Y., T. Ozaki, M. Ouchida, N. Umehara, N. Ohata, A. Yoshida, K. Shimizu, and H. Inoue. 2003. Single nucleotide polymorphism in fibroblast growth factor receptor 4 at codon 388 is associated with prognosis in high-grade soft tissue sarcoma. *Cancer JID*-0374236 98:2245-2250.

Nicholes, K., S. Guillet, E. Tomlinson, K. Hillan, B. Wright, G. D. Frantz, T. A. Pham, L. Dillard-Telm, S. P. Tsai, J. P. Stephan, J. Stinson, T. Stewart, and D. M. French. 2002. A mouse model of hepatocellular carcinoma: ectopic expression of fibroblast growth factor 19 in skeletal muscle of transgenic mice. *Am. J. Pathol.* 160:2295-2307.

Ornitz, D. M., J. Xu, J. S. Colvin, D. G. McEwen, C. A. MacArthur, F. Coulier, G. Gao, and M. Goldfarb. 1996. Receptor specificity of the fibroblast growth factor family. *J. Biol. Chem.* 271:15292-15297.

Reineke U. Antibody epitope mapping using arrays of synthetic peptides. Methods Mol. Biol. 2004; 248:443-63.

Shaoul, E., R. Reich-Slotky, B. Berman, and D. Ron. 1995. Fibroblast growth factor receptors display both common and distinct signaling pathways. *Oncogene* 20; 10:1553-1561.

Skerra A. Engineered protein scaffolds for molecular recognition. J Mol Recognit. 2000 July-August; 13(4):167-87.

St Bernard, R., L. Zheng, W. Liu, D. Winer, S. L. Asa, and S. Ezzat. 2005. Fibroblast growth factor receptors as molecular targets in thyroid carcinoma. *Endocrinology*. 146:1145-1153.

Streit, S., J. Bange, A. Fichtner, S. Ihrler, W. Issing, and A. Ullrich. 2004. Involvement of the FGFR4 Arg388 allele in head and neck squamous cell carcinoma. *Int J Cancer JID*-0042124 111:213-217.

Spinola, M., V. Leoni, C. Pignatiello, B. Conti, F. Ravagnani, U. Pastorino, and T. A. Dragani. 2005. Functional FGFR4Gly388Arg polymorphism predicts prognosis in lung adenocarcinoma patients. *J. Clin. Oncol.* 23:7307-7311.

Streit, S., D. S. Mestel, M. Schmidt, A. Ullrich, and C. Berking. 2006. FGFR4 Arg388 allele correlates with tumour thickness and FGFR4 protein expression with survival of melanoma patients. *Br. J. Cancer*. e-pub ahead of print.

Tangri et al., J Immunol. 2005 Mar. 15; 174(6):3187-96.

Vainikka, S., V. Joukov, P. Klint, and K. Alitalo. 1996. Association of a 85-kDa serine kinase with activated fibroblast growth factor receptor-4. *J. Biol. Chem.* 19; 271:1270-1273.

Vainikka, S., V. Joukov, S. Wennstrom, M. Bergman, P. G. Pelicci, and K. Alitalo. 1994. Signal transduction by fibroblast growth factor receptor-4 (FGFR-4). Comparison with FGFR-1. *J. Biol. Chem.* 269:18320-18326.

Vainikka, S., J. Partanen, P. Bellosta, F. Coulier, D. Birnbaum, C. Basilico, M. Jaye, and K. Alitalo. 1992. Fibroblast growth factor receptor-4 shows novel features in genomic structure, ligand binding and signal transduction. *EMBO J.* 11:4273-4280.

van Heumen, W. R., C. Claxton, and J. O. Pickles. 1999. Fibroblast growth factor receptor-4 splice variants cause deletion of a critical tyrosine. IUBMB. Life 48:73-78.

Wang, J., D. W. Stockton, and M. Ittmann. 2004. The fibroblast growth factor receptor-4 arg388 allele is associated with prostate cancer initiation and progression. Clin. Cancer Res. 10:6169-6178.

Wang S, Diamond D L, Hass G M, Sokoloff R, Vessella R L. Identification of prostate specific membrane antigen (PSMA) as the target of monoclonal antibody 107-1A4 by proteinchip; array, surface-enhanced laser desorption/ionization (SELDI) technology.

Weinstein, M., X. Xu, K. Ohyama, and C. X. Deng. 1998. FGFR-3 and FGFR-4 function cooperatively to direct alveogenesis in the murine lung. Development 125:3615-3623.

Werner S, Smola H, Liao X, et al. The function of KGF in morphogenesis of epithelium and reepithelialization of wounds. Science. 1994; 266:819-822.

Xie, M. H., I. Holcomb, B. Deuel, P. Dowd, A. Huang, A. Vagts, J. Foster, J. Liang, J. Brush, Q. Gu, K. Hillan, A. Goddard, and A. L. Gurney. 1999. FGF-19, a novel fibroblast growth factor with unique specificity for FGFR4. Cytokine JID-9005353 11:729-735.

Yu, C., F. Wang, M. Kan, C. Jin, R. B. Jones, M. Weinstein, C. X. Deng, and W. L. McKeehan. 2000. Elevated cholesterol metabolism and bile acid synthesis in mice lacking membrane tyrosine kinase receptor FGFR4. J Biol Chem JID-2985121R 275:15482-15489.

Zhao, P., G. Caretti, S. Mitchell, W. L. McKeehan, A. L. Boskey, L. M. Pachman, V. Sartorelli, and E. P. Hoffman. 2006. Fgfr4 is required for effective muscle regeneration in vivo. Delineation of a MyoD-Tead2-Fgfr4 transcriptional pathway. J. Biol. Chem. 281:429-438.

The invention claimed is:

1. An isolated antibody that binds to the extracellular domain of FGFR4 or an antigen binding fragment thereof, wherein the antibody or antigen binding fragment comprises at least one heavy chain amino acid sequence comprising the following CDRs:
   a CDRH1 as shown in SEQ ID NO: 9,
   (b) a CDRH2 as shown in SEQ ID NO: 10, and
   (c) a CDRH3 as shown in SEQ ID NO: 11, and
   at least one light chain amino acid sequence comprising the following CDRs:
   a CDRL1 as shown in SEQ ID NO: 12,
   (e) a CDRL2 as shown in SEQ ID NO: 13, and
   a CDRL3 as shown in SEQ ID NO: 14.

2. The antibody of claim 1, which comprises a heavy chain amino acid sequence of SEQ ID NO: 5 or at least the variable domain thereof or an amino acid sequence having an identity of at least 90% thereto, and a light chain amino acid sequence of SEQ ID NO:6 or at least the variable domain thereof or an amino acid sequence having an identity of at least 90% thereto.

3. The antibody according to claim 1, which is a monoclonal antibody, a recombinant antibody, a humanized antibody, a chimeric antibody, a multispecific antibody, or an antigen binding fragment thereof.

4. The antibody according to claim 1, which is a Fab fragment, a Fab' fragment, a F(ab')$_2$ fragment, a Fv fragment, a diabody, or a single chain antibody molecule.

5. The antibody according to claim 1, which is of the IgG1-, IgG2-, IgG3- or IgG4-type.

6. The antibody according to claim 1, which is coupled to a labeling group.

7. The antibody according to claim 6, wherein the labelling group is a radioisotope or radionuclide, a fluorescent group, an enzymatic group, a chemiluminescent group, a biotinyl group, or a predetermined polypeptide epitope.

8. The antibody according to claim 1, which is coupled to an effector group.

9. The antibody according to claim 8, wherein the effector group is a radioisotope or radionuclide, a toxin, or a therapeutic or chemotherapeutic group.

10. A pharmaceutical composition comprising an antibody according to claim 1.

11. The pharmaceutical composition of claim 10 comprising pharmaceutically acceptable carriers, diluents and/or adjuvants.

12. The pharmaceutical composition according to claim 10, optionally comprising a further active agent.

13. A kit comprising an antibody according to claim 1.

14. The kit according to claim 13, further comprising a further antineoplastic agent.

15. An isolated antibody that binds to the extracellular domain of FGFR4 or an antigen binding fragment thereof, wherein the antibody or antigen binding fragment comprises at least one heavy chain amino acid sequence comprising the following CDRs:
   (a) a CDRH1 as shown in SEQ ID NO: 9,
   (b) a CDRH2 as shown in SEQ ID NO: 10, and
   (c) a CDRH3 as shown in SEQ ID NO: 11, and
   at least one light chain amino acid sequence comprising the following CDRs:
   (d) a CDRL1 as shown in SEQ ID NO: 12,
   (e) a CDRL2 as shown in SEQ ID NO: 13, and
   (f) a CDRL3 as shown in SEQ ID NO: 14,
   wherein said antibody reduces or blocks FGFR4 phosphorylation by reducing or blocking FGFR4-mediated signal transduction; said antibody binds to the extracellular domain of FGFR4 at a location which reduces or blocks ligand binding; said antibody inhibits enough FGFR4 activity to reduce or block cell proliferation; and said antibody inhibits enough FGFR4 activity to reduce or block cell migration.

* * * * *

UNITED STATES PATENT AND TRADEMARK OFFICE
CERTIFICATE OF CORRECTION

PATENT NO. : 8,394,927 B2  Page 1 of 1
APPLICATION NO. : 12/513448
DATED : March 12, 2013
INVENTOR(S) : Bange et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this
First Day of September, 2015

Michelle K. Lee
*Director of the United States Patent and Trademark Office*

SEQUENCE LISTING

```
<160> NUMBER OF SEQ ID NOS: 22

<210> SEQ ID NO 1
<211> LENGTH: 408
<212> TYPE: DNA
<213> ORGANISM: Artificial
<220> FEATURE:
<223> OTHER INFORMATION: oligonucleotide sequence encoding heavy chain
      variable region of rat anti-FGFR-4 antibody 10F10 raised against
      the extracellular domain of human FGFR-4

<400> SEQUENCE: 1
atggctgtcc tggtgctgtt gctctgcctg gtgacatttt caagctgtgt cctgtccgag      60
gtgcagctga aggaatcagg acctggtctg gtgcagccct cacagaccct gtccctcacc     120
tgcactgtct ctggattctc attaacggac tacagtgtac actgggttcg ccagcctcca     180
ggaaaaggtc tggagtggat gggagtagtg tggagtagtg gaagtacagc atataattca     240
gctctcaaat cccgactgcg catcaccagg gacacctcca agagccaagc tttcttaaaa     300
atgaacagtc tgcaaactga agacacagcc atttactact gtaccagacc taggtattcc     360
agttggtttg tttactgggg ccaaggcact ctggtcactg tctcttca                  408

<210> SEQ ID NO 2
<211> LENGTH: 378
<212> TYPE: DNA
<213> ORGANISM: Artificial
```

-continued

```
<220> FEATURE:
<223> OTHER INFORMATION: oligonucleotide sequence encoding light chain
      variable region of rat anti-FGFR-4 antibody 10F10 raised against
      the extracellular domain of human FGFR-4

<400> SEQUENCE: 2
atggagacag acagactcct gctatgggtg ctgctgctct gggttccagg ctccactggt      60
gacactgtgc tgacccagtc tcctgctttg gctgtgtctc tagggcagag ggtcaccatc     120
tcttgtaggg ccagcaaaag tgtcagtaca tttattcact ggtaccaaca gaaatcggga     180
cagcaaccca aactcctgat ctatagtgca tccaacacag aatctggacc ttccaggttc     240
agtgggagtg ggtctgggac agactttacc ctcaccatag atcctgtgga ggctgatgac     300
atagcaaact attactgtca gcagagtaat gaacttccgt ggacgttcgg tggaggcacc     360
aagctggaat tgaaacgg                                                   378

<210> SEQ ID NO 3
<211> LENGTH: 411
<212> TYPE: DNA
<213> ORGANISM: Artificial
<220> FEATURE:
<223> OTHER INFORMATION: oligonucleotide sequence encoding heavy chain
      variable region of rat anti-FGFR-4 antibody 9A5 raised against the
      extracellular domain of human FGFR-4

<400> SEQUENCE: 3
atggctgtcc tggtgctgtt gctctgcctg ctgacatttc caagctgtgt cctgtcccag      60
gtgcagctga gggagtcagg acctggtctg gtgcagccct cacagacttt gtctctcacc     120
tgcactgtct ctgggttctc actaaccttc tatcatgtaa gctgggttcg ccagcctcca     180
ggaaaaggtc tggagtggat gggagtaata tggactggtg aagcacaac atataattca      240 cttctcaaat cccgactgac catcagcagg gacacctcca gagccaagt tttcttaaaa      300 atgaacagtc tacaaactga agacacagcc acttactact gtgccagagg ggtggtgac      360 aggggctact ttgccttctg ggcccagga accatggtca ccgtgtcctc a               411

<210> SEQ ID NO 4
<211> LENGTH: 384
<212> TYPE: DNA
<213> ORGANISM: Artificial
<220> FEATURE:
<223> OTHER INFORMATION: oligonucleotide sequence encoding light chain
      variable region of rat anti-FGFR-4 antibody 9A5 raised against the
      extracellular domain of human FGFR-4

<400> SEQUENCE: 4
atggagttaa tcagtcaggt cttcgtattt ctgctgctct ggttgtctgg ggtttatggg      60
aatactgtga tgacccagtc tcccacatct atgttcacat cagtaggaga cagggttacc     120
atgagctgca aggccagtca gaatgtaggt attaatgtag ctggtacca acaaaaaaca      180 gggcagtctc ctaaacggct tatctactgg gcatccaacc gggacactgg ggtccctgat     240
cgcttcacag gcagtggatc tgggacagat ttcactctca ccatcagcaa catgcaggct     300
gaagacccag ctatttacta ctgtctgcag cataactcct atccgtggac gttcggtgga     360
ggcaccaagc tggagctgaa acgg                                            384

<210> SEQ ID NO 5
<211> LENGTH: 136
<212> TYPE: PRT
<213> ORGANISM: Artificial
```

<220> FEATURE:
<223> OTHER INFORMATION: amino acid sequence of heavy chain variable
      region of rat anti-FGFR-4 antibody 10F10 raised against the
      extracellular domain of human FGFR-4

<400> SEQUENCE: 5

Met Ala Val Leu Val Leu Leu Leu Cys Leu Val Thr Phe Ser Ser Cys
1               5                   10                  15

Val Leu Ser Glu Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Asp Tyr Ser Val His Trp Val Arg Gln Pro Pro Gly Lys Gly Leu
    50                  55                  60

Glu Trp Met Gly Val Val Trp Ser Ser Gly Ser Thr Ala Tyr Asn Ser
65                  70                  75                  80

Ala Leu Lys Ser Arg Leu Arg Ile Thr Arg Asp Thr Ser Lys Ser Gln
                85                  90                  95

Ala Phe Leu Lys Met Asn Ser Leu Gln Thr Glu Asp Thr Ala Ile Tyr
            100                 105                 110

Tyr Cys Thr Arg Pro Arg Tyr Ser Ser Trp Phe Val Tyr Trp Gly Gln
        115                 120                 125

Gly Thr Leu Val Thr Val Ser Ser
    130                 135

<210> SEQ ID NO 6
<211> LENGTH: 126
<212> TYPE: PRT
<213> ORGANISM: Artificial
<220> FEATURE:
<223> OTHER INFORMATION: amino acid sequence of light chain variable
      region of rat anti-FGFR-4 antibody 10F10 raised against the
      extracellular domain of human FGFR-4

<400> SEQUENCE: 6

Met Glu Thr Asp Arg Leu Leu Leu Trp Val Leu Leu Trp Val Pro
1               5                   10                  15

Gly Ser Thr Gly Asp Thr Val Leu Thr Gln Ser Pro Ala Leu Ala Val
            20                  25                  30

Ser Leu Gly Gln Arg Val Thr Ile Ser Cys Arg Ala Ser Lys Ser Val
        35                  40                  45

Ser Thr Phe Ile His Trp Tyr Gln Gln Lys Ser Gly Gln Gln Pro Lys
    50                  55                  60

Leu Leu Ile Tyr Ser Ala Ser Asn Thr Glu Ser Gly Pro Ser Arg Phe
65                  70                  75                  80

Ser Gly Ser Gly Ser Gly Thr Asp Phe Thr Leu Thr Ile Asp Pro Val
                85                  90                  95

Glu Ala Asp Asp Ile Ala Asn Tyr Tyr Cys Gln Gln Ser Asn Glu Leu
            100                 105                 110

Pro Trp Thr Phe Gly Gly Gly Thr Lys Leu Glu Leu Lys Arg
        115                 120                 125

<210> SEQ ID NO 7
<211> LENGTH: 137
<212> TYPE: PRT
<213> ORGANISM: Artificial
<220> FEATURE:
<223> OTHER INFORMATION: amino acid sequence of heavy chain variable
      region of rat anti-FGFR-4 antibody 9A5 raised against the
      extracellular domain of human FGFR-4

```
<400> SEQUENCE: 7

Met Ala Val Leu Val Leu Leu Leu Cys Leu Leu Thr Phe Pro Ser Cys
1               5                   10                  15

Val Leu Ser Gln Val Gln Leu Arg Glu Ser Gly Pro Gly Leu Val Gln
                20                  25                  30

Pro Ser Gln Thr Leu Ser Leu Thr Cys Thr Val Ser Gly Phe Ser Leu
            35                  40                  45

Thr Phe Tyr His Val Ser Trp Val Arg Gln Pro Pro Lys Gly Leu
    50                  55                  60

Glu Trp Met Gly Val Ile Trp Thr Gly Gly Ser Thr Thr Tyr Asn Ser
65              70                  75                  80

Leu Leu Lys Ser Arg Leu Thr Ile Ser Arg Asp Thr Ser Lys Ser Gln
                85                  90                  95

Val Phe Leu Lys Met Asn Ser Leu Gln Thr Glu Asp Thr Ala Thr Tyr
            100                 105                 110

Tyr Cys Ala Arg Gly Gly Gly Asp Arg Gly Tyr Phe Ala Phe Trp Gly
            115                 120                 125

Pro Gly Thr Met Val Thr Val Ser Ser
            130                 135

<210> SEQ ID NO 8
<211> LENGTH: 128
<212> TYPE: PRT
<213> ORGANISM: Artificial
<220> FEATURE:
<223> OTHER INFORMATION: amino acid sequence of light chain variable
      region of rat anti-FGFR-4 antibody 9A5 raised against the
      extracellular domain of human FGFR-4

<400> SEQUENCE: 8

Met Glu Leu Ile Ser Gln Val Phe Val Phe Leu Leu Leu Trp Leu Ser
1               5                   10                  15

Gly Val Tyr Gly Asn Thr Val Met Thr Gln Ser Pro Thr Ser Met Phe
                20                  25                  30

Thr Ser Val Gly Asp Arg Val Thr Met Ser Cys Lys Ala Ser Gln Asn
            35                  40                  45

Val Gly Ile Asn Val Gly Trp Tyr Gln Gln Lys Thr Gly Gln Ser Pro
    50                  55                  60

Lys Arg Leu Ile Tyr Trp Ala Ser Asn Arg Asp Thr Gly Val Pro Asp
65              70                  75                  80

Arg Phe Thr Gly Ser Gly Ser Gly Thr Asp Phe Thr Leu Thr Ile Ser
                85                  90                  95

Asn Met Gln Ala Glu Asp Pro Ala Ile Tyr Tyr Cys Leu Gln His Asn
            100                 105                 110

Ser Tyr Pro Trp Thr Phe Gly Gly Gly Thr Lys Leu Glu Leu Lys Arg
            115                 120                 125

<210> SEQ ID NO 9
<211> LENGTH: 10
<212> TYPE: PRT
<213> ORGANISM: Artificial
<220> FEATURE:
<223> OTHER INFORMATION: amino acid sequence of HCDR1 of rat anti-FGFR-4
      antibody 10F10 raised against the extracellular domain of human
      FGFR-4

<400> SEQUENCE: 9

Gly Phe Ser Leu Thr Asp Tyr Ser Val His
1               5                   10
```

```
<210> SEQ ID NO 10
<211> LENGTH: 16
<212> TYPE: PRT
<213> ORGANISM: Artificial
<220> FEATURE:
<223> OTHER INFORMATION: amino acid sequence of HCDR2 of rat anti-FGFR-4
      antibody 10F10 raised against the extracellular domain of human
      FGFR-4

<400> SEQUENCE: 10

Val Val Trp Ser Ser Gly Ser Thr Ala Tyr Asn Ser Ala Leu Lys Ser
1               5                   10                  15

<210> SEQ ID NO 11
<211> LENGTH: 10
<212> TYPE: PRT
<213> ORGANISM: Artificial
<220> FEATURE:
<223> OTHER INFORMATION: amino acid sequence of HCDR3 of rat anti-FGFR-4
      antibody 10F10 raised against the extracellular domain of human
      FGFR-4

<400> SEQUENCE: 11

Arg Pro Arg Tyr Ser Ser Trp Phe Val Tyr
1               5                   10

<210> SEQ ID NO 12
<211> LENGTH: 11
<212> TYPE: PRT
<213> ORGANISM: Artificial
<220> FEATURE:
<223> OTHER INFORMATION: amino acid sequence of LCDR1 of rat anti-FGFR-4
      antibody 10F10 raised against the extracellular domain of human
      FGFR-4

<400> SEQUENCE: 12

Arg Ala Ser Lys Ser Val Ser Thr Phe Ile His
1               5                   10

<210> SEQ ID NO 13
<211> LENGTH: 7
<212> TYPE: PRT
<213> ORGANISM: Artificial
<220> FEATURE:
<223> OTHER INFORMATION: amino acid sequence of LCDR2 of rat anti-FGFR-4
      antibody 10F10 raised against the extracellular domain of human
      FGFR-4

<400> SEQUENCE: 13

Ser Ala Ser Asn Thr Glu Ser
1               5

<210> SEQ ID NO 14
<211> LENGTH: 9
<212> TYPE: PRT
<213> ORGANISM: Artificial
<220> FEATURE:
<223> OTHER INFORMATION: amino acid sequence of LCDR3 of rat anti-FGFR-4
      antibody 10F10 raised against the extracellular domain of human
      FGFR-4

<400> SEQUENCE: 14

Gln Gln Ser Asn Glu Leu Pro Trp Thr
1               5

<210> SEQ ID NO 15
<211> LENGTH: 10
<212> TYPE: PRT
<213> ORGANISM: Artificial
```

```
<220> FEATURE:
<223> OTHER INFORMATION: amino acid sequence of HCDR1 of rat anti-FGFR-4
      antibody 9A5 raised against the extracellular domain of human
      FGFR-4

<400> SEQUENCE: 15

Gly Phe Ser Leu Thr Phe Tyr His Val Ser
1               5                   10

<210> SEQ ID NO 16
<211> LENGTH: 16
<212> TYPE: PRT
<213> ORGANISM: Artificial
<220> FEATURE:
<223> OTHER INFORMATION: amino acid sequence of HCDR2 of rat anti-FGFR-4
      antibody 9A5 raised against the extracellular domain of human
      FGFR-4

<400> SEQUENCE: 16

Val Ile Trp Thr Gly Gly Ser Thr Thr Tyr Asn Ser Leu Leu Lys Ser
1               5                   10                  15

<210> SEQ ID NO 17
<211> LENGTH: 10
<212> TYPE: PRT
<213> ORGANISM: Artificial
<220> FEATURE:
<223> OTHER INFORMATION: amino acid sequence of HCDR3 of rat anti-FGFR-4
      antibody 9A5 raised against the extracellular domain of human
      FGFR-4

<400> SEQUENCE: 17

Gly Gly Gly Asp Arg Gly Tyr Phe Ala Phe
1               5                   10

<210> SEQ ID NO 18
<211> LENGTH: 11
<212> TYPE: PRT
<213> ORGANISM: Artificial
<220> FEATURE:
<223> OTHER INFORMATION: amino acid sequence of LCDR1 of rat anti-FGFR-4
      antibody 9A5 raised against the extracellular domain of human
      FGFR-4

<400> SEQUENCE: 18

Lys Ala Ser Gln Asn Val Gly Ile Asn Val Gly
1               5                   10

<210> SEQ ID NO 19
<211> LENGTH: 7
<212> TYPE: PRT
<213> ORGANISM: Artificial
<220> FEATURE:
<223> OTHER INFORMATION: amino acid sequence of LCDR2 of rat anti-FGFR-4
      antibody 9A5 raised against the extracellular domain of human
      FGFR-4

<400> SEQUENCE: 19

Trp Ala Ser Asn Arg Asp Thr
1               5

<210> SEQ ID NO 20
<211> LENGTH: 9
<212> TYPE: PRT
<213> ORGANISM: Artificial
<220> FEATURE:
<223> OTHER INFORMATION: amino acid sequence of LCDR2 of rat anti-FGFR-4
      antibody 9A5 raised against the extracellular domain of human
      FGFR-4
```

```
<400> SEQUENCE: 20

Leu Gln His Asn Ser Tyr Pro Trp Thr
1               5

<210> SEQ ID NO 21
<211> LENGTH: 36
<212> TYPE: DNA
<213> ORGANISM: Artificial
<220> FEATURE:
<223> OTHER INFORMATION: sense PCR primer for human FGFR-4 extracellular
      region

<400> SEQUENCE: 21
gaattcgcca ccatgcggct gctgctggcc ctgttg                                36

<210> SEQ ID NO 22
<211> LENGTH: 33
<212> TYPE: DNA
<213> ORGANISM: Artificial
<220> FEATURE:
<223> OTHER INFORMATION: antisense PCR primer for human FGFR-4
      extracellular region

<400> SEQUENCE: 22
cgaggccagg tatacggaca tcatcctcga gtt                                   33
```